United States Patent [19]

Anderson

[11] 4,112,191

[45] Sep. 5, 1978

[54] DETOXIFICATION OF LEAD PAINT

[75] Inventor: William S. Anderson, Sunnyvale, Calif.

[73] Assignee: United Technologies Corporation, Hartford, Conn.

[21] Appl. No.: 802,110

[22] Filed: May 31, 1977

[51] Int. Cl.² ................... C07C 155/06; B05D 3/10; B32B 9/00

[52] U.S. Cl. .................. 428/497; 260/429.9; 260/513.5; 427/333; 427/417; 106/287.18; 106/287.25

[58] Field of Search ............. 260/429.9, 513.5; 427/333, 417; 428/497; 106/287 SC

[56] References Cited

U.S. PATENT DOCUMENTS

| | | | |
|---|---|---|---|
| 2,317,765 | 4/1943 | Hester | 260/513.5 X |
| 2,885,416 | 5/1959 | Costabello et al. | 260/513.5 X |
| 3,050,552 | 8/1962 | Nemec et al. | 260/513.5 |

*Primary Examiner*—James R. Hoffman
*Attorney, Agent, or Firm*—Steven F. Stone

[57] ABSTRACT

Lead paint can be extremely hazardous when ingested as a result of ionic lead, produced by the action of stomach acids, being subsequently absorbed into the blood stream. According to this invention, it has been found that certain metal salts of the dithiocarbamates of multifunctional amines are effective precipitants for lead ions. When ingested simultaneously with lead paint they precipitate the lead ion in a substantially insoluble and indigestible form and thereby prevent absorption of lead into the blood stream. The preferred compounds are: zinc pentaerythrityl tetrakis (dithiocarbamate), tetrasodium pentaerythrityl tetrakis (dithiocarbamate), disodium ethylene bis(dithiocarbamate), and zinc ethylene bis(dithiocarbamate). These materials can be included in a digestible coating which can be applied over lead based paints to effectively detoxify the lead paint.

8 Claims, No Drawings

DETOXIFICATION OF LEAD PAINT

GOVERNMENT RIGHTS

The Government has rights in this invention pursuant to Contract Number H-2284R, awarded by the Department of Housing and Urban Development.

BACKGROUND OF THE INVENTION

The hazard of lead poisoning resulting from the ingestion, particularly by children, of lead based paint is well known and very prevalent. Since it would be almost impossible and quite expensive to either remove all of the existing lead based paint which is now on structures through the United States or to cover such structures with a child-proof barrier of plywood or plastic, alternative approaches to the solution of the problem have been investigated. The concept of coating the walls with a material which would be capable of precipitating the lead after it has been ingested by the child had been considered, but to date no material has been found which could safely perform this function. The use of the wide variety of lead precipitants such as calcium sulfide, sodium diethyl dithiocarbamate, British Anti-Lewisite (BAL) (dimercaptopropanol), dimercaptosuccinic acid, dihydrothioctic acid, sodium 2,3-dimercaptopropane sulphonate, potassium methyl and ethylxanthates, sodium alginate or pectate, dithiocarbamate based ion-exchange resins, milk, sodium fluoride, sodium sulfate, sodium phosphate, sodium thiocyanate, sodium sulfide, sodium thiosulfate, sodium alkylxanthates, sodium oxalates, sodium silicate, and sodium alginate or pectate for example have been considered but have been unusable either because the materials themselves are poisonous, the precipitated lead is not sufficiently insoluble either in both aqueous and fat based systems, the precipitation reaction does not go to completion, the precipitant itself is toxic, the materials are unstable either in the conditions of application or subsequent to ingestion, the materials cannot be formed into coating, have high equivalent weights or for some unknown reason as is the case with sodium alginate or pectate the precipitants just do not work in vivo. According to this invention, it has been found that certain metallic salts of the dithiocarbamates of polyfunctional amines of low equivalent weight possess the necessary characteristics of low toxicity, stability, low equivalent weight, completeness of precipitation and non-toxicity of the precipitant that are necessary to a usable material for abatement of lead poisoning. It is accordingly an object of this invention to provide safe effective lead precipitants. It is another object of this invention to provide a digestible coating containing a lead precipitant that can be applied over lead based paint to reduce the hazard of lead poisoning. These and other objects of the invention will be readily apparent from the following descriptions.

DESCRIPTION OF THE INVENTION

According to this invention it has been found that metal salts of dithiocarbamates of multifunctional amines are usable to detoxify lead according to this invention provided they have the following general characteristics:

(1) The precipitant must be non-toxic. This means that the material itself must be non-toxic and not undergo any chemical reaction within the body that would cause the release of toxic by-products.

(2) The precipitant must be stable under the ambient conditions of temperature, humidity and light that are anticipated in the use of the material as a structural coating.

(3) The precipitate obtained by the reaction of the precipitant with free lead ion must be non-toxic within the same criteria as those of the precipitant.

(4) The precipitate should be substantially insoluble in stomach acid and intestinal fluids and other body fluids; and (5) The precipitate should pass through the stomach and intestinal tract without measurable absorption in the blood stream.

The multifunctional amines from which the precipitants of this invention may be derived include, without limitation, hydrazine, ethylene diamine, 1, 2, 3-triaminopropane, triaminoisobutane, diethylene triamine, triethylene tetramine, tetraethylene pentamine, poly (ethyleneimine) of the formula $(-CH_2CH_2NH)_x$ where $x$ is from about 6–100, poly (diaminomethyl) oxetane of the formula

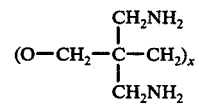

where $x$ is about 6–100, polyvinylamine of the formula

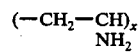

where $x$ is about 2 to 10,000, pentaerythrityl tetramine, dipentaerythritylhexamine, and tripentaerythrityl octamine, diaminomethane and hexahydrotriazine for example. (The latter two multifunctional amines are not stable per se but their carbon disulfide adducts are.) Suitable metal salts include the alkali metals such as sodium and potassium and the alkaline earth metals such as magnesium and calcium, which produce salts which are generally water soluble. Zinc and magnesium produce salts which are generally water insoluble. The latter are in some cases preferred since these materials are not readily leached from the coating or soluble in gut fluids but are still capable of undergoing ion exchange with lead. In view of the large number of individual materials which can be reacted to produce precipitants according to this invention, it is quite apparent that not all combinations of materials will be effective. In general, the alkali metal salts such as the sodium and potassium salts tend to be less stable in air or tend to undergo undesirable decomposition in gut fluid. However, as will be apparent below one of the preferred embodiments of this invention is in fact a sodium salt which has unexpectedly good stability. With respect to the insoluble compounds, non-crystalline materials are preferred over crystalline materials in that it has been observed that ion exchange proceeds more rapidly and completely with the non-crystalline materials than with the crystalline materials.

The precipitants of this invention can be mixed with any number of binders which are attacked by stomach acid quickly. Suitable binders include casein, soybean, polyvinyl alcohol, starch, gelatin, xanthan gum and methyl cellulose binders and paint binders of the acrylic, vinyl, styrene-butadiene, and alkyd type for example which may in addition contain conventional paint pigments such as titanium dioxide, calcium carbonate, zinc oxide and barium sulfate for example.

Within the broad class of materials defined above I have found that the preferred embodiments, at this time, are: sodium ethylene-bis (dithiocarbamate) and zinc ethylene-bis (dithiocarbamate) (these materials are commercially available as agricultural fungicides under the names NABAM and ZINEB, respectively), tetrasodium pentaerythrityl tetrakis (dithiocarbamate) and zinc pentaerythrityl tetrakis (dithiocarbamate). Having thus generally described my invention, the following specific examples are provided.

The precipitant should be present in about twice the amount theoretically sufficient to react with all lead present. (See Example IV and Example IX.)

EXAMPLE I

PREPARATION OF TETRASODIUM PENTAERYTHRITYL TETRAKIS (DITHIOCARBAMATE)

The general reaction scheme by which this material is prepared from pentaerythrityl tetramine is as follows:

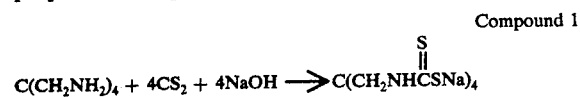

Compound 1

Owing to yield reducing side reactions, simple mixing of the tetramine with four equivalents of carbon disulfide and sodium hydroxide does not produce a satisfactory yield. Compound 1 has been prepared as follows:

16.1 grams (0.212 mols) of carbon disulfide and five milliliters of pyridine were placed in a 100 milliliter three-necked Morton flask equiped with a mechanical stirrer, reflux condenser and two addition funnels. Three drops of 1% phenolphthalein were added and the reaction flask was placed in an ice bath. 3.5 grams (0.0265 mols) of distilled pentaerythrityl tetramine dissolved in 7 milliliters of pyridine were slowly added with vigorous stirring. A precipitate formed immediately. The reaction flask was removed from the ice bath and three molar aqueous sodium hydroxide was slowly added until the pink color appeared. After a reaction period of several minutes, the pink color disappeared; sodium hydroxide solution was again added with continuous vigorous stirring until the pink color reappeared. This process was repeated until a total 34.5 milliliters (0.106 mols) of sodium hydroxide solution was added. At this point the orange reaction mixture contained two liquid layers and no solid material. The reaction mixture was then evaporated to dryness on a vacuum rotary evaporator and the solid residue recrystalized from ethanol to give 14.0 grams of colorless crystals. The NMR of the recrystalized material indicated its composition to be $C(CH_2NHCS_2Na)_4 \cdot 8.5\ H_2O$. The 14 grams thus corresponds to a yield of 78% of the theoretical.

EXAMPLE II

PREPARATION OF ZINC PENTAERYTHRITYL TETRAKIS (DITHIOCARBAMATE)

This material may be produced from Compound 1 according to the following reaction sequence:

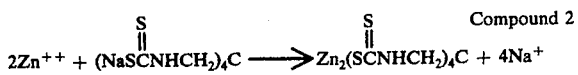

Compound 2 can be produced by the addition of one equivalent of zinc ion in acidic solution to an aqueous solution of Compound 1. This produces almost immediately a white finely divided precipitate with the yield being about 99% of that calculated for the reaction. In this regard it was observed that the reaction was independent of the order of the mixing of the reactants. It is well known in dithiocarbamate fungicide manufacturing that the yield and solubility of products obtained from the addition of zinc ion to difunctional dithiocarbamates depends on the order of addition of the reactants. Addition of the sodium salt to excess zinc ion leads to a lower molecular weight, partially water soluble product whereas reversing this mixing order forms a higher molecular weight water insoluble material. The contrast with respect to the reaction shown above is easily explained in terms of coordination polymerization. The difunctional dithiocarbamates used in the manufacture of fungicides can form only linear polymers by reaction with zinc while the tetrafunctional dithiocarbamate analogs can yield an insoluble three dimensional network at any zinc to sodium charge ratio above 1 to 4.

EXAMPLE III

The resistance to oxidation and stability of Compound 1 was determined by passing air through an aqueous concentrated solution of Compound 1 at room temperature for several hours and by heating compound 1 for two weeks in a stream of air at 60° C. In both of these tests no discoloration or precipitation of compound 1 and no change in the infrared spectrum or NMR pattern was observed. The refractory nature of compound 1 is substantially better than NABAM, another sodium based detoxifier within the scope of this invention, and other potential detoxifiers such as selenocysteamine, mercaptans, amines and phenols.

EXAMPLE IV

An aqueous solution of compound 1 was added to a dilute, acidified solution (pH 2-3) containing lead ion. A flocculent light yellow precipitate was obtained immediately according to the following reaction:

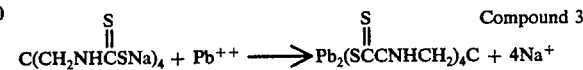

Compound 3

The precipitate is insoluble in chloroform, ether, pyridine, twelve molar and one molar hydrochloric acid, one molar sodium bicarbonate, one molar glycine, and one molar sodium chloride. From the insolubility of this compound under these conditions it was predicted that the material would not be assimilated into the blood stream when administered orally to animals and this prediction was verified as set forth below. In strong hot sodium hydroxide compound 3 is converted to a black solid, probably lead sulfide. In strong hot ethylene diamine tetra acetic acid (EDTA) solution at pH 8 it is dissolved; and except for oxidizing acids, concentrated EDTA at this pH is the only solvent for compound 3 known at present. The x-ray diffraction pattern of the precipitated compound 3 does not reveal any ordered phases and it is therefore suspected that the structure of this precipitate is that of a three dimensional glass-like network containing tetrafunctional crosslinks.

EXAMPLE V

Stirring basic lead carbonate with a solution of compound 1 converts part of the lead to the dithiocarbamate according to the following reaction:

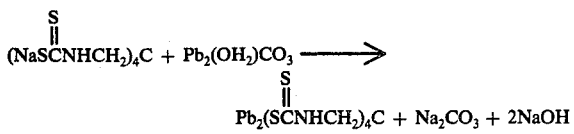

Conversion under these conditions is at best only 10–20% and the product, compound 3, is converted in part to a black solid, probably PbS, by the strong caustic generated during the reaction. Accordingly, compound 1 is considered to be a more effective lead precipitant in acid solution that it is in basic solutions and this is consistent with its use in the stomach.

EXAMPLE VI

Compound 2 was stirred with 0.001 molar lead nitrate and was converted to compound 3 even though both compound 2 and compound 3 are essentially insoluble in water. The reaction was followed potentiometrically with a lead specific electrode and conversion was 99% complete in less than 5 hours at 25° C at pH 2.

EXAMPLE VII

The effectiveness and toxicity of materials according to this invention were determined by studies in rats in which the materials shown in Table 1 were administered to rats and measurements were taken to determine various types of absorption and the routes by which the materials are eliminated. The rats were housed in stainless steel cages, provided with a chow (0.2 ppm lead) and water and were quarantined for four days before the start of the tests. Mean rat weights were 83 grams at the start of the dosage and 165 grams at the end of two weeks of dosing; growth was normal for the strain of rats used (Charles River CD). One rat from group 4 died early in the test from unknown causes. The doses were selected so as to furnish about 10 milligrams of lead each day to each rat in groups 2, 3 and 4. Expressed as a function of body weight the doses were: group 2 – 195 milligrams of lead acetate per kilo; group 3 – 256 milligrams of compound 2 per kilogram; group 4 – 195 milligrams of lead acetate per kilo followed by 213 milligrams per kilo of compound 1 decahydrate; and group 5 – 213 milligrams of compound 1 decahydrate per kilo.

After completion of the experimental regime for a period of two weeks the animals were sacrificed, dissected and the parts examined for lead content by atomic absorption spectroscopy. Neither the animal pathologist nor spectroscopist were aware of the composition or the dosage administered. The results are shown in Table 1. From these tests the following conclusions were drawn:

(1) Large repeated oral doses of compound 3 (which contains 49% lead by weight) do not measurably elevate the lead concentration in blood, urine, femur, liver or kidneys. Essentially all the lead in the oral doses is excreted in the feces.

(2) Dosing with an equivalent amount of lead acetate markedly raises lead levels in blood, urine, femur and internal organs.

(3) Dosing with lead acetate then with one equivalent of compound 1 raises lead levels to about half the concentration resulting from administrating lead acetate alone. Since compound 3 passes through the gut without absorption the failure of compound 1 to deactivate 100% of the ingested lead acetate was probably due to incomplete capture of lead ion by compound 1. This may be partially due to a portion of compound 1 being involved in the capture of other materials such as iron, magnesium, zinc cobalt and copper. Although these materials can be displaced by lead, the dwell time in the gut may be insufficient for equilibrium to be reached and a higher dosage of compound 1 is indicated to drive the lead precipitation reaction to completion.

EXAMPLE VIII

Two commercially available dithiocarbamate fungicides, disodium ethylene bis (dithiocarbamate), Nabam, and the corresponding zinc salt zinc ethylene bis (dithiocarbamate), Zineb, were investigated as precipitants according to this invention. Both of these materials have been in use for many years as agricultural fungicides and toxicity studies of both Nabam and Zineb indicate that these materials are sufficiently safe to permit ingestion by humans. The $LD_{50}$ in rats of Nabam is about 395 mg/kg while the $LD_{50}$ of Zineb in rats is greater than 5200 mg/kg. At a coverage of 13 mg Zineb per square centimeter for example a 25 kilogram child would need to ingest 10,000 square centimeters of coating at one sitting in order to reach the 5200 mg/kg dose.

The lead analog of Nabam was produced by adding, with stirring, 0.01 mol (3.31 grams) of lead nitrate dissolved in one liter of water, adjusted to pH 2 with hydrochloric acid, to 0.01 mols (6.70 grams) of sodium ethylene bis(dithiocarbamate) hexahydrate, obtained by evaporating a 22% solution of commercial Nabam, dissolved in 100 ml of water. The precipitate was collected on a glass frit, washed with 50 ml of 0.01 molar hydrochloric acid and with four 200 ml portions of deionized water. Further washing at that point gave a wash liquid which yielded no visible precipitate when saturated with hydrogen sulfide. From past experience it was known that lead content of the wash water was therefore less than two ppm. The precipitate, dried at room temperature under vacuum weighed 4.22 grams; theoretical weight being 4.17 grams (0.01 mol of lead

TABLE 1

| Rat Group | Daily Dose | Blood Lead, mg/100 ml | Urine ppm Pb | Feces, ppm Pb | Femur, ppm Pb | Liver, ppm Pb | Kidney, ppm Pb |
|---|---|---|---|---|---|---|---|
| 1 | Water Only | 8.7 ± 5.3 | 0.60 | 14 | 11.3 ± 3.0 | 1.9 ± 1.9 | 1.1 ± 0.5 |
| 2 | Lead acetate | 35.5 ± 38.0 | 1.7 | 4200 | 100.5 ± 67.5 | 2.8 ± 2.7 | 27.7 ± 8.5 |
| 3 | Compound 3 | 7.2 ± 2.9 | 0.4 | 3700 | 11.6 ± 5.0 | 1.5 ± 1.8 | 1.1 ± 0.6 |
| 4 | Lead acetate followed by Compound 1 | 18.8 ± 12.2 | 0.9 | 4900 | 42.4 ± 8.5 | 3.0 ± 1.8 | 7.6 ± 3.8 |
| 5 | Compound 1 only | 11.7 ± 10.8 | 1.2 | 10 | 17.0 ± 3.1 | 1.4 ± 0.9 | 1.3 ± 1.0 | ethylene bis(dithiocarbamate)(LEBD). The solubility of LEBD in various media was determined by adding thereto an aqueous solution containing sufficient LEBD (0.03 grams) to yield 5000 ppm of lead upon complete hydrolysis. The lead concentration in the solution was determined and results are shown in Table I.

TABLE 1

Solubility of Lead Ethylene Dithiocarbamate in Aqueous Reagents

| Reagent | Lead Concentration, ppm in Solution after 3 days |
|---|---|
| Hydrochloric acid, 1 molar | 7.8 |
| Glycine, 1 molar | 0.3 |
| Sodium chloride, 1 molar | 0.9 |
| Sodium bicarbonate, 1 molar | 9.1 |
| Water (deionized) | 0.1 |

EXAMPLE IX

The preceding example employed LEBD obtained from a lead precipitant, Nabam, which was water soluble. Zineb, a water insoluble material, also undergoes ion exchange with lead. To demonstrate this, 0.5250 grams of Zineb was combined with 0.6325 grams of lead nitrate and the two dry powders were ground together in a mortar. A few milliliters of water were then added and mixed well with the solids to dissolve the lead nitrate. Color change was observed immediately. Nitric acid, 0.1%, was added dropwise to adjust the pH to 3.0. The mixture was ground again for a few minutes, then allowed to stand for one hour interrupted with 3-5 minutes of grinding at 15-minute intervals. The yellow solid formed was transferred to a tared, medium porosity, sintered glass crucible and washed with water until the wash liquid yielded neither a color nor a precipitate when diluted Nabam was added. The product, when dried to constant weight, weighed 0.7694 grams, which is 96.6% of the weight calculated for complete ion exchange. The solubility of the LEBD produced according to this ion exchange reaction was determined in a manner similar to that for Example VIII and the results are shown in Table II.

TABLE II

Solubility Of Lead Ethylene Dithiocarbamate (Derived By Ion Exchange) in Aqueous Reagents

| | Zinc ppm in Solution | Lead, ppm in Solution after standing overnight |
|---|---|---|
| Water | 1.2 | 44 |
| Hydrochloric acid, 1 molar | 19.5 | 116 |
| Sodium bicarbonate, 1 molar | 3.6 | 24 |
| Sodium chloride, 1 molar | 1.3 | 2.1 |
| Glycine, 1 molar | 1.3 | 14 |
| Chloroform | 0.06 | 2 |

The only known solvents for LEBD are the oxidizing acids (hot nitric or perchloric) and aqueous EDTA at pH 8-9. At this pH the lead-EDTA complex has its greatest stability; the stability of the lead-EDTA complex evidently exceeds that of the dithiocarbamate complex in this pH range. At acidic pH levels, however, LEBD is not attacked by EDTA; in strong acid (pH 2) EDTA is instead precipitated as the free acid.

EXAMPLE X

A commercial casein-based film forming preparation (Borden Chemical ST-227) which is a solution of ammonium caseinate containing preservatives and some other additives and sold as an additive for polyvinyl acetate latex; was mixed in various proportions with Zineb to determine the film forming characteristics. The pure casein material dries in air with a weight loss of approximately 80% leaving a transparent, nearly colorless, water-repellent film having 1H pencil hardness. This dry film disintegrates on standing one hour in 0.01 normal hydrochloric acid at 25° C or on standing overnight in 5% sodium bicarbonate solution. The film, however, can be soaked in water for several days with little swelling and without detachment from a glass substrate. The characteristics of various portions of Zineb and Borden films are described in Table III.

TABLE III

Properties Of Paint Films Prepared From Zineb And Borden ST-227

| Parts by Weight | | |
|---|---|---|
| Zineb | Borden ST-227 | |
| 3 | 1 | chalky "orange peel" effect |
| 2 | 1 | good hiding power slightly chalky good brushability |
| 1 | 1 | good hiding power non-chalky |
| 1 | 2 | adequate hiding power better film strength |

After soaking for 1-2 hours in 0.01 normal hydrochloric acid these coatings crumble with the touch. Higher Zineb/binder ratios favor fast disintegration in acid while a low ratio favors higher film strength but lower hiding power. A reasonable compromise is a one-to-two weight ratio of Zineb to ST-227.

EXAMPLE XI

Various other binders were considered. Their evaluation is set forth below.

TABLE IV

| Material | Suitability Factors |
|---|---|
| Polyvinyl alcohol | Forms surface coatings of high mechanical strength, inert toward dithiocarbamates and cures with only trace amounts of borax. Cured films can be washed with water without dissolving but swell quickly in 0.1 normal hydrochloric acid. Soluble material in the film should be released in the stomach when ingested, although the film itself does not dissolve. Films of polyvinyl alcohol are paintable with acrylic latex. |
| Xanthan gum | Forms tough clear films which are instantly cured by spraying with ferric sulfate solution. The cured film resists alkali but dissolves in dilute aqueous acid and is paintable with latex. Disadvantage is any ferric ion remaining from the curing solution will be captured by free dithiocarbamate and would necessarily require more dithiocarbamate to effectively detoxify lead. |
| Methylcellulose films | Undesirable - film is not as strong as polyvinyl alcohol and requires cure time of many days with melamine/ |

TABLE IV-continued

| Material | Suitability Factors |
|---|---|
| | formaldehyde or urea/formaldehyde resin. The resulting film dissolves very slowly in 0.1 molar hydrochloric acid which makes it undesirable for prompt release of material in the stomach. |
| Polyethylene oxide | Undesirable - although a familiar medium for pharmacological administration of drugs and an aqueous solution of 4000 molecular weight dries to a waxy film which is soluble rapidly in water; the material does not contain sufficient functionality to permit a good cure. |
| Acrylic latex house paint (Sherman Williams A-100 latex) in which the emulsifier is of the anionic type | Tolerates sodium dithiocarbamates without coagulation, and, as can be seen from Example XII, rapidly releases dithiocarbamates upon exposure to acid solution. Soluble precipitants such as Nabam may leached out of the paint film by soaking in water and thus it would not retain any Nabam in humid locations or in locations which are washed. Acrylic latex house paint however should be good for insoluble precipitants such as Zineb. |

EXAMPLE XII

One gram of Nabam was mixed with 5 ml of latex paint and spread on glass with an 8 mil doctor blade and allowed to dry. When soaked for one hour in 0.1 normal hydrochloric acid at 37° C, the resulting paint film lost 25% of its wieght, a figure corresponding to extraction of essentially all of the dithiocarbamate content under these simulated stomach conditions. If this extraction is performed in an acidic solution containing lead ion, LEBD starts to precipitate immediately. A visual experiment involves immersion of a lead-based paint film into a beaker of 0.1 normal hydrochloric acid and a film of Nabam-doped paint in a beaker of 0.1 normal hydrochloric acid. When either film alone is immersed, no precipitate occurs, however, when both films are simultaneously immersed, a flocculent light yellow precipitate of LEBD forms immediately.

This invention has been described with respect to several embodiments thereof, however, these embodiments are exemplary rather than limiting. Various modifications to the invention will suggest themselves to workers skilled in the art which can be made without departing from the scope of this invention which is limited only by the following claims wherein:

I claim:

1. A method for reducing the hazard of lead poisoning which comprises coating a surface having a lead based paint applied thereon with a material selected from the group consisting of the alkali metal, alkaline earth metal and zinc salts of dithiocarbamates of multifunctional amines which materials are:
   (a) non-toxic;
   (b) stable under the ambient conditions of temperature, humidity and light; and
   (c) capable of forming a lead precipitate which is non-toxic, substantially insoluble in body fluids and capable of passing through the stomach and intestinal tract of a mammalian subject without measurable absorption in the bloodstream;
   in amounts sufficient to precipitate substantially all of the lead contained in the paint on said surface.

2. The method of claim 1 wherein said material is selected from the group consisting of Nabam, Zineb, tetradosium pentaerythrityl tetrakis (dithiocarbamate) and zinc pentaerythrityl tetrakis (dithiocarbamate).

3. A composition of matter consisting of a film forming binder having dispersed therein a material selected from the group consisting of the alkali metal and alkaline earth metal salts of dithiocarbamates of multifunctional amines, said binder being non-toxic and capable of releasing said material in a mammalian stomach after ingestion and said material being:
   (a) non-toxic;
   (b) stable under the ambient conditions of temperature, humidity and light; and
   (c) capable of forming a lead precipitate which is non-toxic, substantially insoluble in body fluids and capable of passing through the stomach and intestinal tract of a mammalian subject without measurable absorption in the bloodstream.

4. A composition of matter of claim 3 wherein said material is selected from the group consisting of Nabam, Zineb, tetrasodium pentaerythrityl tetrakis (dithiocarbamate) and zinc pentaerythrityl tetrakis (dithiocarbamate).

5. A painted surface having lead based paint thereon and containing as a coating thereover the composition of claim 4.

6. A painted surface having lead based paint thereon and containing as a coating thereover the composition of claim 3.

7. Tetrasodium pentaerythrityl tetrakis (dithiocarbamate).

8. Dizinc pentaerythrityl tetrakis (dithiocarbamate).

* * * * *